United States Patent [19]

Poenitsch

[11] Patent Number: 4,649,910
[45] Date of Patent: Mar. 17, 1987

[54] ORTHOPEDIC STOCKING

[75] Inventor: Rick W. Poenitsch, Milwaukee, Wis.

[73] Assignee: Meridian Industries Inc., Milwaukee, Wis.

[21] Appl. No.: 739,524

[22] Filed: May 31, 1985

[51] Int. Cl.$^4$ .............................................. A61F 13/00
[52] U.S. Cl. ...................................................... 128/165
[58] Field of Search ............... 128/82, 87 R, 161, 162, 128/153, 157, 159, 165, 132 R, 132 O, 382, 453, DIG. 20, 15, 24; 29/235; 2/239

[56] References Cited

U.S. PATENT DOCUMENTS

| 3,540,441 | 11/1970 | Collins | 128/165 X |
| 3,934,582 | 1/1976 | Gorrie | 128/157 |
| 4,153,054 | 5/1979 | Boone | 128/157 X |

Primary Examiner—Gregory E. McNeill
Attorney, Agent, or Firm—Andrus, Sceales, Starke & Sawall

[57] ABSTRACT

An orthopedic stocking, comprising a tubular elastic sheath having closed ends and formed with a fenestration adjacent a first of said ends. The stocking is folded in a manner such that the second closed end is drawn through the sheath and projects through the fenestration in the first end to provide overlapping sections. The overlapping sections are then reverse folded to form an outer cuff disposed outwardly of the overlapping sections. To apply the stocking to an extremity, such as a leg, the toe is inserted into the closed second that projects through the fenestration, and the cuff is unrolled upwardly along the limb. After the cuff is unrolled, the corners or ears of the first end are grasped and pulled upwardly to roll the stocking along the limb and the fenestration is sealed to the limb. The stocking provides a sterile seal to the limb to prevent cross contamination.

3 Claims, 7 Drawing Figures

ORTHOPEDIC STOCKING

BACKGROUND OF THE INVENTION

When draping a limb, such as a leg, for surgery, the practice has been to cover the lower leg with a special orthopedic stocking. In the past, the stocking has taken the form of a knitted tube closed at one end and rolled down to resemble a donut. In use, the toe is inserted in the closed end and the stocking is then rolled up over the leg. In some cases the stocking is rolled to a location just below the knee, and the remaining roll of stocking is then taped to the leg below the knee. In other situations the stocking is rolled upwardly above the knee and an opening is cut at the knee through which the surgery is to be performed. The portion of the stocking bordering the opening is then taped to the leg.

The knitted orthopedic stocking has distinct disadvantages. When the stocking is cut, fibres are released causing a particulate problem. Further, in the presence of irrigating solutions, the knitted stocking is wetted through and thus ceases to be an effective bacteria barrier.

In an effort to deal with this problem, orthopedic stockings have utilized a rubberized plastic material as an outer layer over the knitted stocking. The use of the impervious plastic material is effective against moisture coming from the outside. However, it is not effective against moisture running down the leg and entering from the inside. As it is difficult to fully seal the stocking to the leg below the knee, irrigating solution running down the leg will enter the stocking and the liquid will be trapped in the stocking. When the stocking becomes soaked and the foot and toe area fill with liquid, the leg becomes very heavy and is difficult to manipulate during surgery. Moreover, the fact that the fluid can enter the stocking from the top negates the reason for employing the plastic outer sheath, such reason being to keep the stocking dry in order to act as a bacteria barrier.

SUMMARY OF THE INVENTION

The invention is directed to an improved orthopedic stocking that is easy to apply and provides a moisture-proof seal around the limb. In accordance with the invention, the stocking includes a tubular, impervious, elastic sheath having closed ends and provided with a single opening or fenestration adjacent a first of the ends. The sheath is folded in a manner such that the second closed end is drawn inwardly through the sheath and projects through the fenestration in the first end to provide overlapping sections. The overlapping sections are then reverse-folded to form an outer cuff disposed outwardly of the overlapping sections.

To apply the stocking to an extremity such as a leg, the toe is inserted into the closed second end which projects through the fenestration, and the cuff is then unrolled upwardly along the leg. After the cuff has been unrolled, the corners or ears of the first end are grasped and pulled upwardly to unroll the stocking along the leg to the desired location with the fenestration being sealed to the limb.

The fenestration provides a positive seal to the limb to prevent irrigation liquids from flowing downwardly into the stocking. By keeping the limb dry, bacteria migration through a wet drape is prevented. The positive seal of the stocking to the leg also prevents fluid build-up in the foot of the stocking with its resultant weight.

Because the stocking is composed solely of an elastic, impervious plastic material, there is no problem of linting or fibre release as with stockings that utilize a knitted fabric.

As the fenestration seals tightly against the limb, there is no requirement for taping of the stocking to the leg.

The stocking is of less expensive construction than conventional orthopedic stockings and can be readily by the surgeon.

Other objects and advantages will appear in the course of the following description.

DESCRIPTION OF THE DRAWINGS

The drawings illustrate the best mode presently contemplated of carrying out the invention.

In the drawings.

DESCRIPTION OF THE PREFERRED EMBODIMENT

The invention is directed toward an improved orthopedic stocking 1 which can serve as a drape for a limb 2, such as a leg or arm, during surgical procedures. In addition, the stocking can be used to protect a cast on a limb from impregnation by water or other elements.

Figure 1:
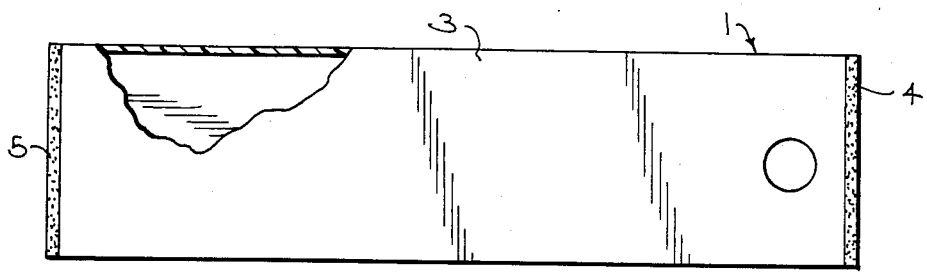
FIG. 1 is a plan view of the orthopedic stocking in the unfolded condition.

In the unfolded condition, as shown in FIG. 1, the stocking 1 consists of a tubular sheath 3 formed of an impervious elastomeric material such as a thermoplastic rubber sold under the tradename Kraton by Shell Oil Company, Houston, Texas. Sheath 3 has a first closed end 4, and a second closed end 5, and a single fenestration or opening 6, normally having a diameter of about 2 inches, is located adjacent the end 4.

Figure 2:
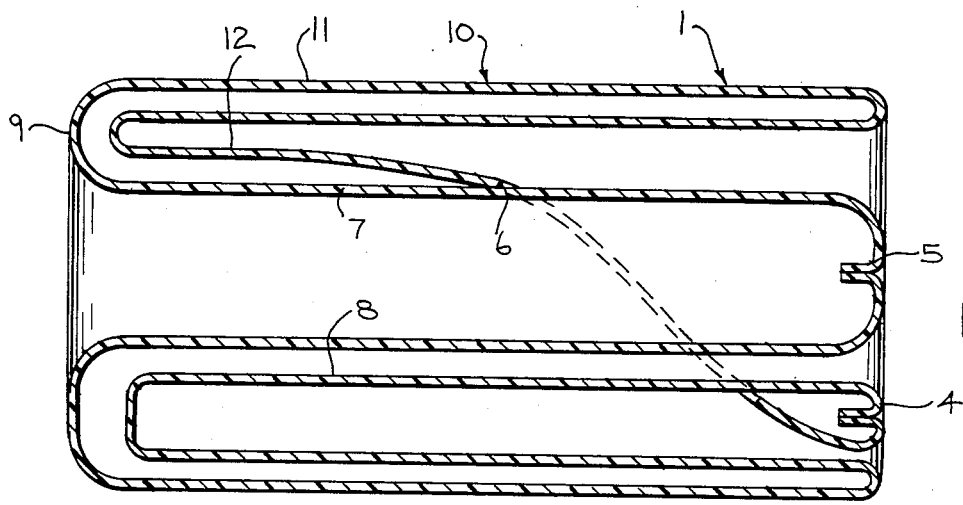
FIG. 2 is a longitudinal section of the orthopedic stocking in the folded condition.

FIG. 2 is a longitudinal section showing the orthopedic stocking in the folded condition. In this folded condition, the end, 5, has been drawn inwardly within the tubular sheath 3, and pulled through the fenestration 6. In this condition, the portion 7 of sheath 3 located adjacent end 5 is in lapping relation with the portion 8 that terminates in the closed end 4.

Figure 3:
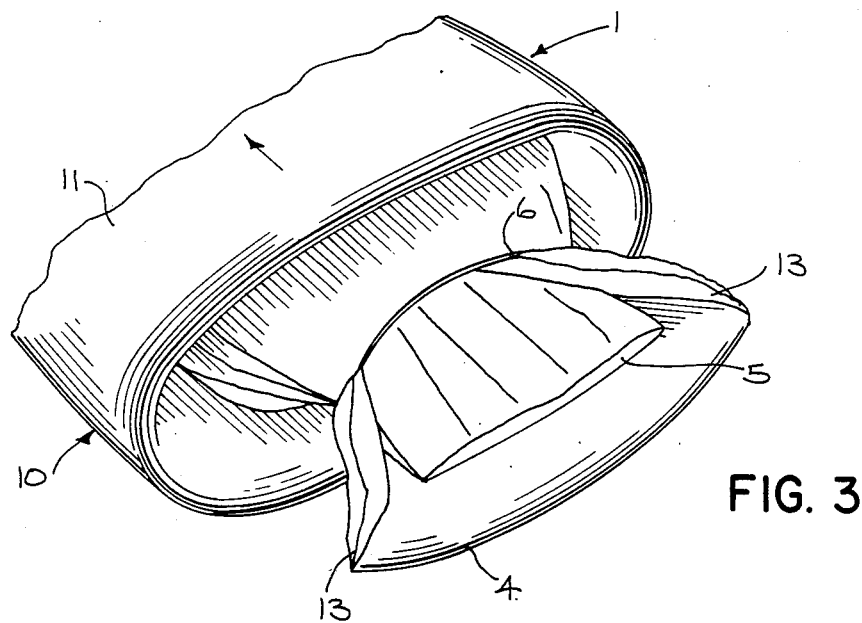
FIG. 3 is a perspective view of the end of the folded stocking.
Figure 4:
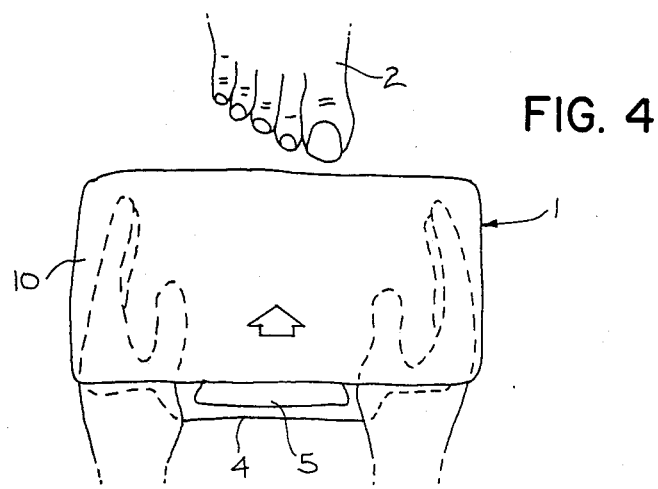
FIG. 4 is a view showing a foot being inserted in the folded stocking as the initial step in applying the stocking to the limb.

Sheath 3 is also provided with a reverse fold as indicated by 9 to provide a cuff 10 that is located outwardly of the overlapping sections 7 and 8. Cuff 10 includes an outer portion 11, which is a continuation of a portion 7, and an inner section 12 which is a continuation of portion 8. As shown in FIG. 3, the corners 13 of closed end 4 are located generally in alignment with the second closed end 5 of cuff 10.

The orthopedic stocking 1 is packaged in the sterile, folded condition, as shown in FIG. 2, and FIGS. 4–7 show the manner in which the stocking is applied to a limb, 2, such as a leg.

After the stocking is removed from its wrapping, the hands are slipped under the cuff 10, as shown in FIG. 3, and the stocking is placed over the foot with the toes disposed in the closed end 5. The hands are then moved upwardly along the leg to unroll the cuff 10.

Figure 5:
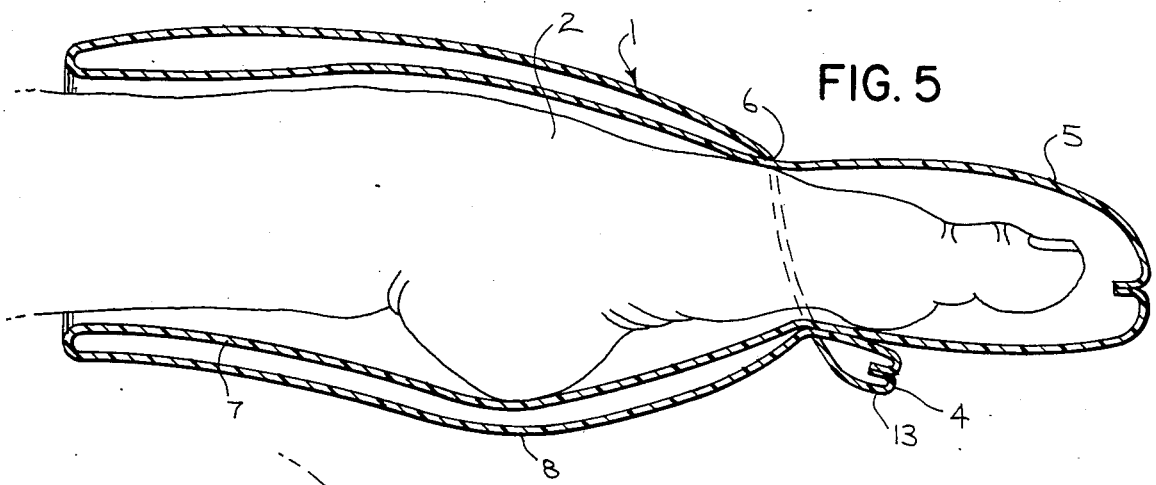
FIG. 5 is a view taken along line 5—5 of FIG. 6 and showing the application of the stocking after unfolding of the cuff.
Figure 6:
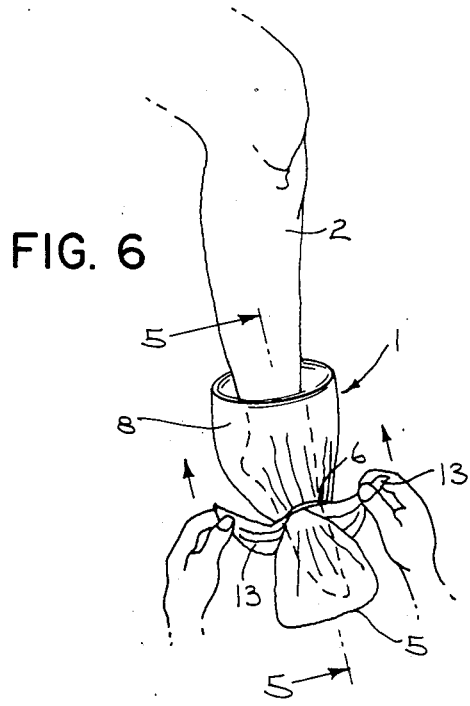
FIG. 6 is a view showing the unrolling of the stocking with the corners of the stocking being pulled upwardly.
Figure 7:
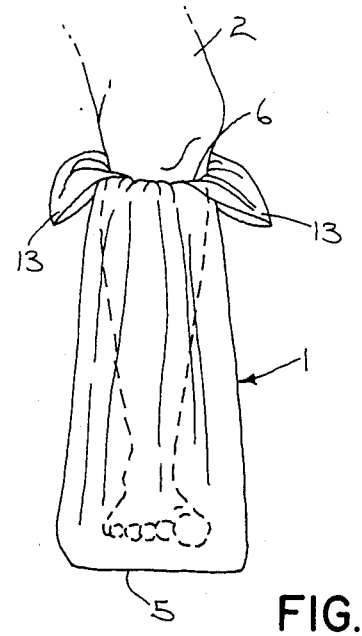
FIG. 7 is a view showing the stocking completely assembled with the leg.

After the cuff 10 is fully unrolled, as shown in FIG. 5, the corners 13 are then grasped, as illustrated in FIG. 6, and pulled upwardly to unroll the stocking along the leg 2. With the stocking just below the surgical site, as illustrated in FIG. 7, the two corners 13 are pulled slightly downward to complete the seal of the fenestration 6 around the limb.

The orthopedic stocking of the invention can be quickly applied to the limb and creates a moisture-proof seal adjacent the surgical site. By keeping the limb dry, bacteria migration is prevented as well as fluid build-up in the foot of the stocking.

As the orthopedic stocking does not include knitted materials, problems of linting and fibre release are eliminated.

Various modes of carrying out the invention are contemplated as being within the scope of the following claims particularly pointing out and distinctly claiming the subject matter which is regarded as the invention.

I claim:

1. An orthopedic stocking, comprising a tubular, elastic impervious sheath, having a first closed end and a second closed end and having a fenestraction adjacent said first end, said second end extending through the sheath and projecting through said fenestration and said first and second ends being disposed in general alignment, portions of said sheath extending from said first and second ends being disposed in overlapping relation.

2. The orthopedic stocking of claim 1, wherein said overlapping portions are folded in a reverse fold to provide an outer cuff disposed outwardly of said overlapping portions.

3. An orthopedic stocking, comprising a tubular elastic impervious sheath having a first end portion terminating in a first closed end and having a second end portion terminating in a second closed end, said first end portion having a fenestration adjacent said first end, said sheath having a generally rectangular configuration in the unfolded flat condition, said sheath being folded in a configuration in which the second end portion is disposed in lapping relation within the first end portion and said second end projects outwardly through said fenestration, the extemity of a limb being adapted to be inserted in said second portion and in engagement with said second end, the corners of said first end being pulled upwardly along the limb to unroll the sheath along the limb and said fenestration providing a tight seal around the limb.

* * * * *